United States Patent [19]

Takahashi

[11] Patent Number: 5,050,585
[45] Date of Patent: Sep. 24, 1991

[54] SHEATHED ENDOSCOPE

[75] Inventor: Nagashige Takahashi, Tokyo, Japan

[73] Assignee: Asahi Kogaku Kogyo Kabushiki Kaisha, Tokyo, Japan

[21] Appl. No.: 552,328

[22] Filed: Jul. 13, 1990

Related U.S. Application Data

[63] Continuation-in-part of Ser. No. 436,130, Nov. 14, 1989, abandoned, which is a continuation of Ser. No. 328,511, Mar. 24, 1989, abandoned.

[30] Foreign Application Priority Data

Mar. 28, 1988 [JP]  Japan ................................ 63-74129

[51] Int. Cl.$^5$ ................................................ A63B 1/00
[52] U.S. Cl. .................................................... 128/4
[58] Field of Search ....................................... 128/4, 6

[56] References Cited

U.S. PATENT DOCUMENTS

| | | | |
|---|---|---|---|
| 4,616,631 | 10/1986 | Takahashi | 128/6 |
| 4,646,722 | 3/1987 | Silverstein et al. | 128/4 |
| 4,741,326 | 5/1988 | Sidall et al. | 128/4 |

Primary Examiner—William H. Grieb
Attorney, Agent, or Firm—Sandler, Greenblum, & Bernstein

[57] ABSTRACT

A sheathed endoscope having a flexible insert tube in the form of an elongated cylinder and a distal end portion with a viewing window which is coupled to the distal end of the insert tube. The endoscope includes: a flexible guide tube inserted in the insert tube so as to extend over the entire length of the insert tube with, one end of the guide tube opening to the outside at the distal end portion and the other end of the guide tube opening to the outside at the proximal end of the insert tube. A sheath which is transparent at least partially thereof which is positioned over the surface of the viewing window and the sheath is removably fitted over the insert tube to isolate the insert tube from the external environment. At least one channel tube inserted in the sheath so as to extend over the entire length of the sheath, one end of the channel tube opening to the outside at the distal end portion of the sheath, and the other end of the channel tube being inserted into the guide tube from the distal end thereof and drawn out of the proximal end of the guide tube.

11 Claims, 3 Drawing Sheets

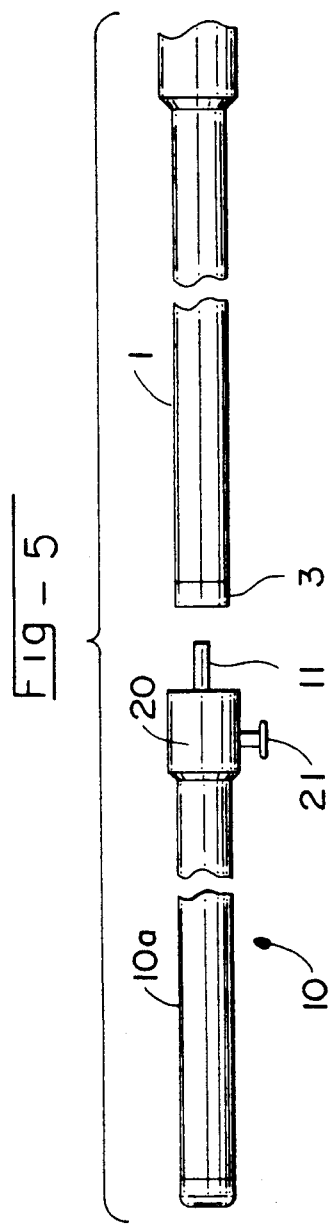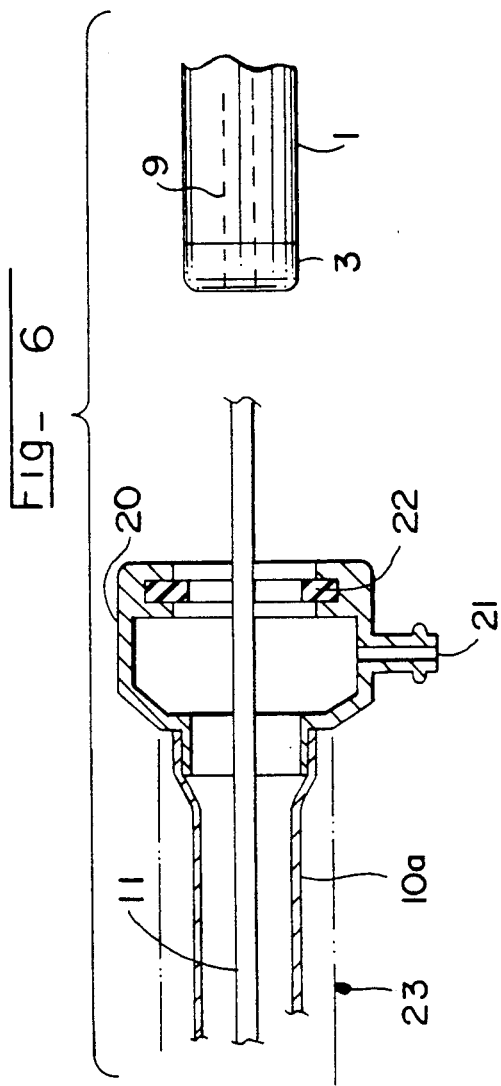

SHEATHED ENDOSCOPE

This application is a continuation-in-part of application Ser. No. 07/436,130, filed Nov. 14, 1989, which is a continuation of Ser. No. 07/328,511 filed Mar. 24, 1989, both now abandoned.

BACKGROUND OF THE INVENTION

1. Field of the Invention

The present invention relates to an endoscope which is inserted into a hollow organ of the body undergoing examination. More particularly, the present invention pertains to a sheathed endoscope which is designed so that a portion thereof which comes into contact with mucus and mucous membrane in a hollow organ of the patient's body can be disposed of after being used for one endoscopic procedure.

To entirely prevent the transmission of bacteria and viruses from one patient to another through an endoscope, it is most effective to arrange an endoscope such that a portion thereof which comes into contact with mucus and mucous membrane in a hollow organ of the patient's body can be disposed of after being used for one endoscopic procedure.

Among various portions that constitute in combination an endoscope, those which come into contact with mucus and mucous membrane in a hollow organ of the patient's body include the outer surface of the insert tube and channels such as biopsy, air and water channels. Therefore, not only the skin of the insert tube but also these channels need to be made disposable so that they are disposed of after use.

2. Description of the Related Art

FIG. 4 shows a conventional sheathed endoscope wherein a U-shaped groove 52 is axially formed in the outer surface of an insert tube 51 of the endoscope and the outer surface of the insert tube 51 is covered with a removable sheath 53. Further, a channel tube 54 is fitted into the groove 52 from the outer side of the insert tube 51 so that both the sheath 53 and the channel tube 54 are disposable (see U.S. Pat. No. 4,646,722).

The above-described prior art suffers, however, from the following problems. Since the channel tube 54 is fitted in the U-shaped groove 52 formed in the outer surface of the insert tube 51, when the insert tube 51 is bent to have a small radius of curvature, the channel tube 54 protrudes outward from the groove 52; in some cases, the channel tube 54 comes out of the groove 52, which may result in damage to the channel tube 54 and the sheath 53. In addition, since it is essential for the insert tubes of endoscopes to have high torsional and crushing strengths as well as high flexibility, spiral tubes are generally employed for the insert tubes of endoscopes. In actual practice, however, it is almost impossible to form a U-shaped groove such as the groove 52 shown in FIG. 4 in the outer surface of a spiral tube. Accordingly, it has heretofore been impossible to produce a practicable flexible tube in regard to the structure in which a channel tube is fitted into the U-shaped groove 52 from the outer side of the insert tube.

SUMMARY OF THE INVENTION

An object of the present invention is to provide a practical sheathed endoscope having an insert tube which is capable of stably retaining therein a channel tube and which can readily be produced.

Other objects and advantages of the present invention will become apparent from the following detailed description of an illustrated embodiment of the invention.

According to the present invention, there is provided a sheathed endoscope having a flexible insert tube in the form of an elongated cylinder and a distal end portion with a viewing window which is coupled to the distal end of the insert tube. The endoscope comprises a flexible guide tube inserted in the insert tube so as to extend over the entire length of the insert tube, one end of the guide tube opening to the outside at the distal end portion, and the other end of the guide tube opening to the outside at the proximal end of the insert tube. A sheath which is transparent at at least one portion thereof which is positioned over the surface of the viewing window, the sheath being removably fitted over the insert tube to isolate the insert tube from the external environment. At least one channel tube inserted in the sheath so as to extend over the entire length of the sheath, one end of the channel tube opening to the outside at the distal end portion of the sheath, and the other end of the channel tube being inserted into the guide tube from the distal end thereof and drawn out of the proximal end of the guide tube.

In addition, there is provided a sheathed endoscope having a flexible insert tube comprising a flexible guide tube inserted in the insert tube so as to extend over the entire length of the insert tube, one end of the guide tube opening to the outside at the distal end portion, and the other end of the guide tube opening to the outside at a control part of the endoscope. At least one channel tube is also provided, with one end of the channel tube opening to the outside at the distal end portion of the sheath, and the other end of the channel tube being inserted into the guide tube from the distal end thereof and drawn out of the proximal end of the guide tube.

DESCRIPTION OF THE DRAWINGS

The present invention may be more fully understood from the description of a preferred embodiment of the invention set forth below, together with the accompanying drawings, in which:

FIG. 5 is a side view of the sheath prior to insertion over the end of the endoscope; and FIG. 6 is a close-up side view of FIG. 5 showing the sheath ready for insertion over the end of the endoscope via the use of compressed air.

DESCRIPTION OF THE EMBODIMENT

One embodiment of the present invention will be described hereinafter in detail with reference to the accompanying drawings.

Figure 1:
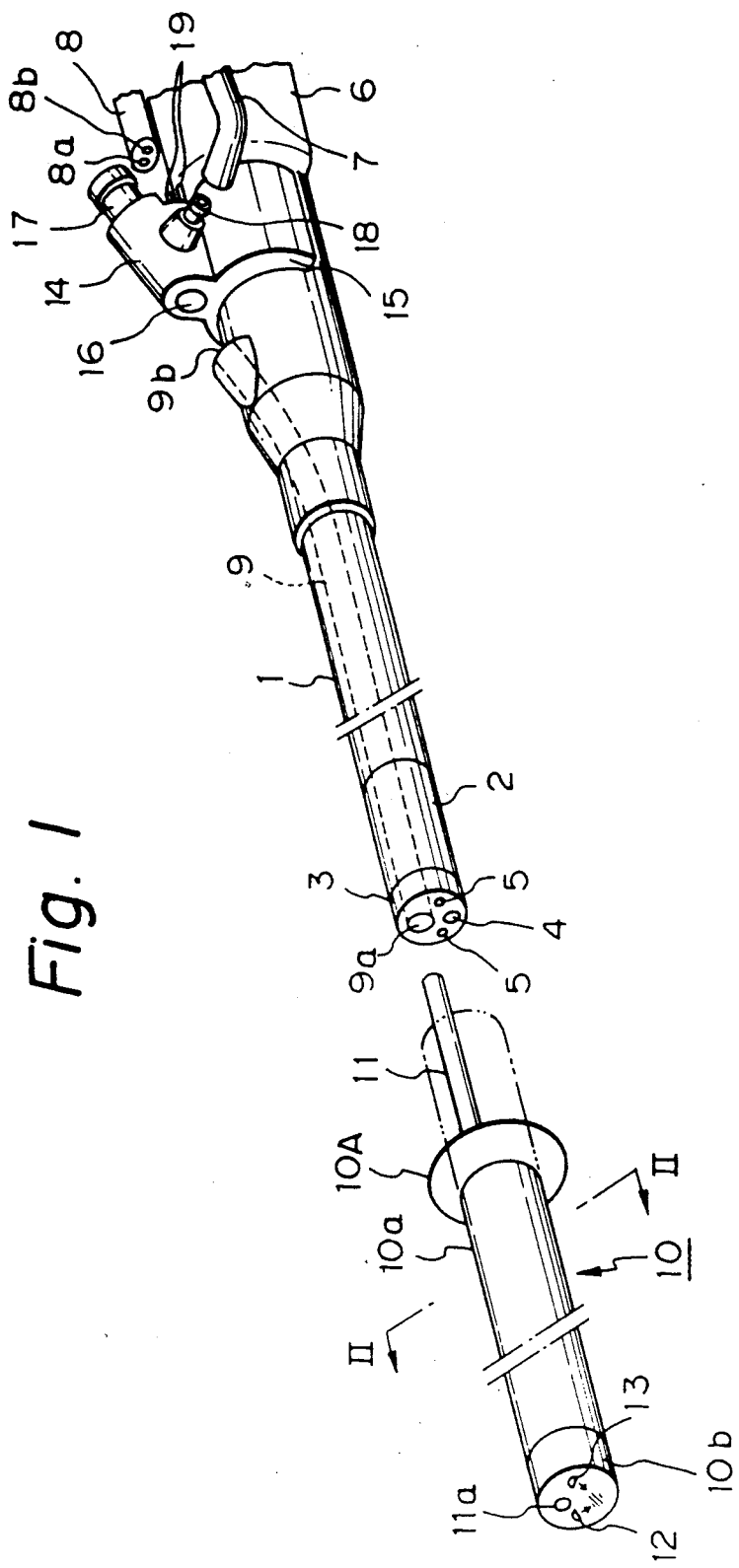
FIG. 1 is a perspective view of one embodiment of the present invention.

FIG. 1 is a perspective view of one embodiment of the sheathed endoscope according to the present invention, which shows particularly the insert part of the endoscope. The reference numeral 1 in the figure denotes an insert tube formed from an elongated cylindrical flexible tube. The insert tube 1 has a bendable portion 2 formed at the distal end thereof, the portion 2 being bendable by remote control. A distal end portion 3 is coupled to the distal end of the bendable portion 2. A viewing window 4 and illuminating windows 5 are formed in the surface of the distal end portion 3. The endoscope of this embodiment is an end-viewing endoscope and therefore the viewing window 4 and the illuminating windows 5 are provided on the front side of the distal end portion 3. An objective lens is disposed at the inner side of the viewing window 4, and the incident end face of an image guide fiber bundle is disposed at the imagery position of the objective lens. The emergent end face of an illuminating light guide is disposed at the inner side of each illuminating window 5. Illustration of these optical means is, however, omitted.

The reference numeral 6 denotes a control part which is coupled to the proximal end portion of the insert tube 1. The control part 6 is provided with a bending control device for controlling bending of the bendable portion 2 and air and water control valves for controlling the supply of air and water, together with a suction control valve. Illustration of these control means is, however, omitted.

The reference numeral 7 denotes a suction pipe which is connected to the suction control valve (not shown). The numeral 8 denotes an air and water pipe which is connected to both the air and water control valves (not shown). The pipe 8 has an air conduit 8a and a water conduit 8b which are provided therein in parallel.

A flexible guide tube 9 which is formed from, for example, a polyethylene tube, extends through the insert tube 1 over the entire length thereof. The distal end 9a of the guide tube 9 opens to the outside at the distal end portion 3 side by side with the viewing window 4, while the proximal end 9b thereof opens to the outside at the lower end portion of the control part 6 in the vicinity of the proximal end of the insert tube 1.

The reference numeral 10 denotes a sheath which is removably fitted over the insert tube 1 so as to isolate it from the external environment. The sheath 10 comprises a tubular portion 10a which is formed in the shape of a thinwalled cylinder using an elastic material, for example, silicone rubber, and a support member 10b which is formed from a transparent material, with both for example, a transparent styrol resin material, with both the tubular portion 10a and the support member 10b being watertightly connected together.

The tubular portion 10a of the sheath 10 has a diameter slightly smaller than the outer diameter of the insert tube 1. The tubular portion 10a of the sheath 10 is readily fitted over the outer surface of the insert tube 1 by virtue of its elasticity, that is, by rolling up the tubular portion 10a into an annular configuration and then unrolling it over the insert tube 1. The tubular portion 10a of the sheath 10 is also readily removed from the outer surface of the insert tube 1 by reversing the above-described procedure. Alternatively, the tubular portion 10a of the sheath 10 is inserted into a somewhat thick tubular member (not shown) and the area between the tubular member and the tubular portion 10a of the sheath 10 is evacuated by means of a vacuum pump or the like. In consequence, the tubular portion 10a expands until it comes into close contact with the inner wall of the thick tubular member. Therefore, in this state, the tubular portion 10a of the sheath 10 is slipped on or off the insert tube 1. If pressurized air is supplied into the sheath 10, neither a tubular member (not shown) nor vacuum pump is needed.

FIGS. 5 and 6 show a sheath according to the present invention for insertion over the insert end of the endoscope by the use of compressed air. In FIG. 5 the tubular portion 10A of the sheath 10 is provided at one end thereof with a manifold 20, which is provided with an air supply nipple 21. As shown in FIG. 6, which manifold 20 is provided with packing 22 so that it can hermetically seal the outer periphery of the insert tube 1. Further, a tubular sheath cover member 23 is inserted over the outside of the tubular portion 10A of the sheath 10. The tubular sheath cover member 23 prevents bursting of the sheath when the sheath is inflated by the pressurized air, supplied through the air supply nipple 21. Since the application of pressurized air through the nipple 21 into the manifold and into the tubular portion 10A of the sheath 10, will cause the expansion or inflation of the tubular portion 10A beyond its normal size, the insertion thereof over the insert end of the endoscope 1 is facilitated.

The support member 10b is formed with such a size that the distal end portion 3 is loosely fitted therein. The support member 10b is provided with two nozzles 12 and 13 which are directed toward that portion of the support member 10b which is positioned over the viewing window 4 when the distal end portion 3 is inserted.

Figure 2:
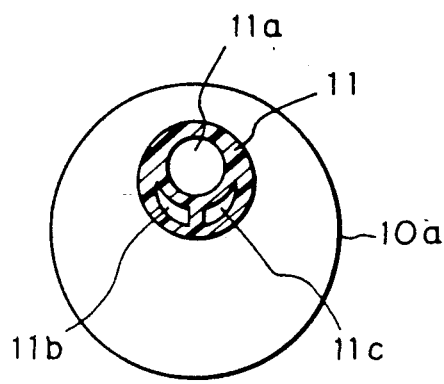
FIG. 2 is a sectional view taken along the line II—II of FIG. 1.
Figure 4:
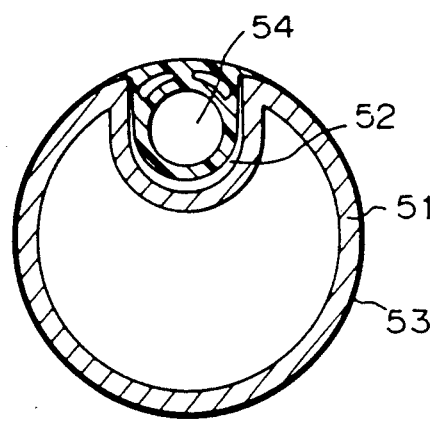
FIG. 4 is a sectional view of a prior art sheathed endoscope.

A channel tube 11 which is made of, for example, tetrafluoroethylene resin, extends through the sheath 10 over the entire length thereof. The channel tube 11 includes a biopsy channel 11a also serving as a suction channel, an air channel 11b and a water channel 11c, as shown in FIG. 2. The biopsy channel 11a is connected to the support member 10b so as to open forward. Accordingly, it is possible to manipulate a forceps or other similar means through the biopsy channel for taking biopsies. The air and water channels 11b and 11c are communicated with the nozzles 12 and 13, respectively, so that the surface of the support member 10b in front of the viewing window 4 can be washed with pressurized air and water.

The channel tube 11 can be inserted into and removed from the guide tube 9 as desired. When the sheath 10 is to be installed on the insert tube 1, one end of the channel tube 11 is inserted into the distal end 9a of the guide tube 9 and drawn out of the proximal end 9b of the guide tube 9.

A connecting adapter 14 for connection of the air, water and suction conduits is detachably attached to the lower end portion of the control part 6. The connecting adapter 14 has a leg 15 made of a synthetic resin material, the leg 15 having a configuration similar to that of one half of a ring. The connecting adapter 14 is attached to the lower end portion of the control part 6 by means of the resilient force from the leg 15 which is forced to expand so as to fit on the lower end portion of the control part 6.

Figure 3:
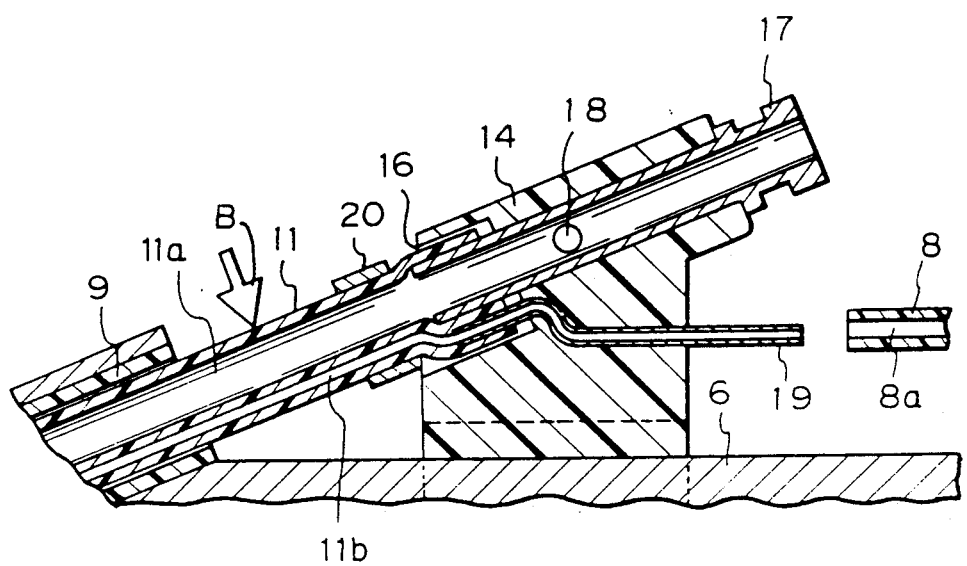
FIG. 3 is a sectional view of a channel tube connected to a connecting adapter.

FIG. 3 shows the channel tube 11 with one end thereof drawn out of the guide tube 9. The connecting adapter 14 will be further explained with reference to FIGS. 1 and 3.

The connecting adapter 14 is formed with a socket 16 with which the channel tube 11 drawn out of the guide tube 9 is connected in such a manner as to extend straight, thus enabling a forceps inserting mouthpiece 17 and the biopsy channel 11a to be connected together coaxially and in a straight-line form. A suction mouthpiece 18 projects sideward from the intermediate portion of the forceps inserting mouthpiece 17, the mouthpiece 18 being communicated with the hollow inside of the mouthpiece 17. The suction pipe 7 is connected to the suction mouthpiece 18.

The air channel 11b and the water channel 11c are connected to respective connecting pipes 19 which are, in turn, connected to the air conduit 8a and the water conduit 8b, respectively. The reference numeral 20 denotes a ring for tightening the mouth portion of the channel tube 11 so that the channel tube 11 is prevented from coming off the connecting adapter 14.

In the actual use of the sheathed endoscope of this embodiment arranged as detailed above, the channel tube 11 is inserted into the guide tube 9 in the state shown in FIG. 1. Then, the tubular portion 10a of the sheath 10 is fitted over the insert tube 1 and the distal end portion 3 is fitted into the support member 10b, thus enabling the insert tube 1 and the distal end portion 3 to be entirely isolated from the external environment. With the endoscope assembled in this way, an object of examination is illuminated with light from the illuminating windows 5 through the transparent support member 10b of the sheath 10. The image of the object thus illuminated enters the objective lens through the viewing window 4.

On the other hand, the suction pipe 7 and the air and water pipe 8 are connected through the connecting adapter 14 to the end portion of the channel tube 11 that is drawn out of the proximal end 9b of the guide tube 9 in the manner described above. Thus, it is possible to effect suction from the support member 10b through the biopsy channel 11a and spray pressurized air and water on the surface of the support member 10b through the air and water channels 11b and 11c. If a forceps or other similar means is inserted from the forceps inserting mouthpiece 17, it is possible to carry out an endoscopic procedure, for example, to take biopsies, through the biopsy channel 11a. Thus, since during the suction operation, the supply of air and water and the bioptic procedure are conducted through the channel tube 11 that is connected to the sheath 10, the guide tube 9 inside the insert tube 1 will not come into contact with the mucus or the mucous membrane inside a hollow organ of the patient's body.

After the use of the endoscope, the channel tube 11 is detached from the connecting adapter 14, the sheath 10 is removed from the insert tube 1 and then the channel tube 11 is drawn out of the guide tube 9. It should be noted that the sheath 10 and the channel tube 11 may be simultaneously removed from the guide tube 9.

However, when the channel tube 11 is drawn out of the guide tube 9, there is a possibility that mucus left inside the channel tube 11 will contaminate the interior of the guide tube 9. Therefore, the channel tube 11 may be fusion-cut at the position indicated by the arrow B in FIG. 3 with the channel tube 11 being left connected to the connecting adapter 14. The cut portion of the channel tube 11 is fusion-bonded by the heat applied during the fusion cutting process and the end of the channel tube 11 is thereby closed. Therefore, if the channel tube 11 which is in this state is drawn out of the guide tube 9, the interior of the guide tube 9 will not be contaminated. The connecting adapter 14 may also be arranged to be disposable after being used for one endoscopic procedure.

According to the present invention, the portion of the endoscope which comes into contact with mucus and mucous membrane inside a hollow organ of the patient's body can be disposed of after being used for one endoscopic procedure and it is therefore possible to prevent transmission of bacteria and viruses from one patient to another. Further, since the guide tube that guides channels is disposed inside the insert tube of the endoscope, the insert tube of the endoscope may be formed in the shape of a simple elongated cylinder. Accordingly, an insert tube which is similar to those which are employed for conventional endoscopes can be employed to produce a sheathed endoscope and this facilitates the production thereof. Thus, the present invention eliminates the problems which have heretofore been experienced in production of an endoscope having an insert tube with a U-shaped groove.

Since the channel tube is inserted in the guide tube disposed inside the insert tube, even if the insert tube is bent to have a small of radius curvature in the clinical use of the endoscope, there is no danger that the channel tube will stick out of the insert tube and invite damage to various portions. Accordingly, the sheathed endoscope of the present invention also has excellent durability.

While the invention has been described by reference to a specific embodiment chosen for purposes of illustration, it should be apparent that numerous modifications could be made thereto by those skilled in the art without departing from the basic concept and scope of the invention.

What is claimed is:

1. A sheathed endoscope having a flexible insert tube in the form of an elongated cylinder having proximal and distal ends, and a distal end portion with a viewing window which is coupled to the distal end of said insert tube, said endoscope comprising:

a flexible guide tube inserted in said insert tube so as to extend over the entire length of said insert tube, one end of said guide tube opening to the outside at said distal end portion, and the other end of said guide tube opening to the outside at the proximal end of said insert tube;

a sheath which is transparent at least a portion thereof which is adapted to be positioned over the surface of said viewing window, said sheath adapted to be positioned over the surface of said viewing window, said sheath adapted to be removably fitted over said insert tube to isolate said insert tube from the external environment; and at least one channel tube inserted in said sheath so as to extend through the entire length of said sheath, one end of said channel tube opening to the outside at the distal end portion of said sheath, and the other end of said channel tube being inserted into said guide tube at the distal end of said guide tube and drawn out of the proximal end of said guide tube.

2. A sheathed endoscope according to claim 1, wherein said sheath has a tubular portion formed in the shape of a thin-walled cylinder of an elastic material and a support member of a transparent material of such a size that said distal end portion of said insert tube is loosely fitted therein, said tubular portion and said support member being watertightly connected together.

3. A sheathed endoscope according to claim 2, wherein said tubular portion has a diameter slightly smaller than the outer diameter of said insert tube, said tubular portion being capable of being rolled up into an annular configuration so that it can be removably fitted over said insert tube.

4. A sheathed endoscope according to claim 2, wherein said tubular portion has a diameter slightly smaller than the outer diameter of said insert tube, said tubular portion being expanded and slipped on or off said insert tube when the area around said tubular portion is decompressed or pressurized air is supplied into said sheath.

5. A sheathed endoscope according to claim 1, wherein said channel tube includes a biopsy channel for inserting a forceps or other similar means.

6. A sheathed endoscope according to claim 5, wherein said biopsy channel is connected to the distal end of said sheath so as to open to the outside thereat.

7. A sheathed endoscope according to claim 1, wherein said channel tube includes a channel for supplying at least air or water to the distal end of said sheath.

8. A sheathed endoscope according to claim 7, wherein the distal end of said sheath is provided with a nozzle which opens toward the outer surface of said transparent portion, said channel communicating with said nozzle.

9. A sheathed endoscope according to claim 1, wherein an end portion of a conduit for passing a fluid is disposed near the proximal end portion of said channel tube drawn out of said guide tube and connecting means is provided for detachably connecting together the end portion of said conduit and the proximal end portion of said channel tube in such a manner that said conduit and said channel tube are communication with each other.

10. A sheathed endoscope according to claim 9, wherein said connecting means is an adapter which is detachable with respect to said endoscope.

11. A sheathed endoscope having a flexible insert tube comprising:

a flexible guide tube inserted in said insert tube so as to extend over the entire length of said insert tube; the distal end of said guide tube opening to the outside of the distal end portion of said insert tube, and the proximal end of said guide tube opening to the outside at a control part of said endoscope; and at least one channel tube, one end of said channel tube opening to the outside at the distal end portion of said guide tube, and the other end of said channel tube being inserted into said guide tube from the distal end thereof and drawn out of the promixal end of said guide tube.

* * * * *